(12) United States Patent
An et al.

(10) Patent No.: US 11,584,913 B2
(45) Date of Patent: Feb. 21, 2023

(54) PSEUDOMONAS AERUGINOSA WITH MONOMETHYLAMINE DEGRADABILITY AND APPLICATION THEREOF

(71) Applicant: GUANGDONG UNIVERSITY OF TECHNOLOGY, Guangdong (CN)

(72) Inventors: Taicheng An, Guangdong (CN); Shiai Li, Guangdong (CN); Guiying Li, Guangdong (CN)

(73) Assignee: GUANGDONG UNIVERSITY OF TECHNOLOGY, Guangzhou (CN)

( * ) Notice: Subject to any disclaimer, the term of this patent is extended or adjusted under 35 U.S.C. 154(b) by 485 days.

(21) Appl. No.: 16/621,206

(22) PCT Filed: Mar. 20, 2018

(86) PCT No.: PCT/CN2018/079528
§ 371 (c)(1),
(2) Date: Dec. 10, 2019

(87) PCT Pub. No.: WO2019/029164
PCT Pub. Date: Feb. 14, 2019

(65) Prior Publication Data
US 2020/0308535 A1    Oct. 1, 2020

(30) Foreign Application Priority Data
Aug. 8, 2017 (CN) .......................... 201710670248.2

(51) Int. Cl.
| C02F 3/34 | (2006.01) |
| C12N 1/20 | (2006.01) |
| B01D 53/72 | (2006.01) |
| B01D 53/84 | (2006.01) |
| B09C 1/10 | (2006.01) |
| C02F 101/38 | (2006.01) |
| C12R 1/385 | (2006.01) |

(52) U.S. Cl.
CPC .............. *C12N 1/20* (2013.01); *B01D 53/72* (2013.01); *B01D 53/84* (2013.01); *B09C 1/10* (2013.01); *C02F 3/34* (2013.01); *C12N 1/205* (2021.05); *B01D 2251/95* (2013.01); *B01D 2257/704* (2013.01); *C02F 2101/38* (2013.01); *C12R 2001/385* (2021.05)

(58) Field of Classification Search
CPC .... C12N 1/20; C12N 1/205; C12R 2001/385; B01D 53/72; B01D 53/84
See application file for complete search history.

(56) References Cited

U.S. PATENT DOCUMENTS
4,490,471 A    12/1984   Ghisalba et al.

FOREIGN PATENT DOCUMENTS
| CN | 1563356 A | 1/2005 |
| CN | 101531969 A | 9/2009 |

OTHER PUBLICATIONS

Eady et al., "Purification and Properties of an Amine Dehydrogenase from Pseudomonas AM1 and its Role in Growth on Methylamine", Biochem. J. 106:245-255, 1968 (Year: 1968).*
EMBL Database Accession No. KJ188250, Nov. 2014, 2 pages (Year: 2014).*
Jahns et al., "Uptake and metabolism of methylammonium by Pseudomonas aeruginosa", FEMS Microbiol. Lett. 72:131-136, 1990 (Year: 1990).*
Chinese-language International Search Report and Written Opinion issued in counterpart PCT Application No. PCT/CN2018/079528 dated May 7, 2018 with English translation (twelve (12) pages).

* cited by examiner

*Primary Examiner* — David Steadman
(74) *Attorney, Agent, or Firm* — Nexsen Pruet, LLC; Todd A. Serbin

(57) ABSTRACT

The present invention discloses a strain of *Pseudomonas aeruginosa* with monomethylamine degradability and the application thereof. This strain, named *Pseudomonas aeruginosa* GDUTAN1, was deposited on May 24, 2017 in the China Center for Type Culture Collection in Wuhan University, Wuhan City, Hubei Province with a deposit number of CCTCC NO.: M 2017283. This *Pseudomonas aeruginosa* GDUTAN1 was Gram-negative and rod-like, and round, green and opaque in the colony morphology, having a diameter of 1-2 mm. The *Pseudomonas aeruginosa* GDUTAN1 of the present invention can be applied to environmental remediation, degrading monomethylamine in the environment at a high degradation efficiency. When it degrades monomethylamine for 96 h at a substrate concentration of 50-140 mg/L, the degradation efficiency can reach more than 99%.

2 Claims, 1 Drawing Sheet
Specification includes a Sequence Listing.

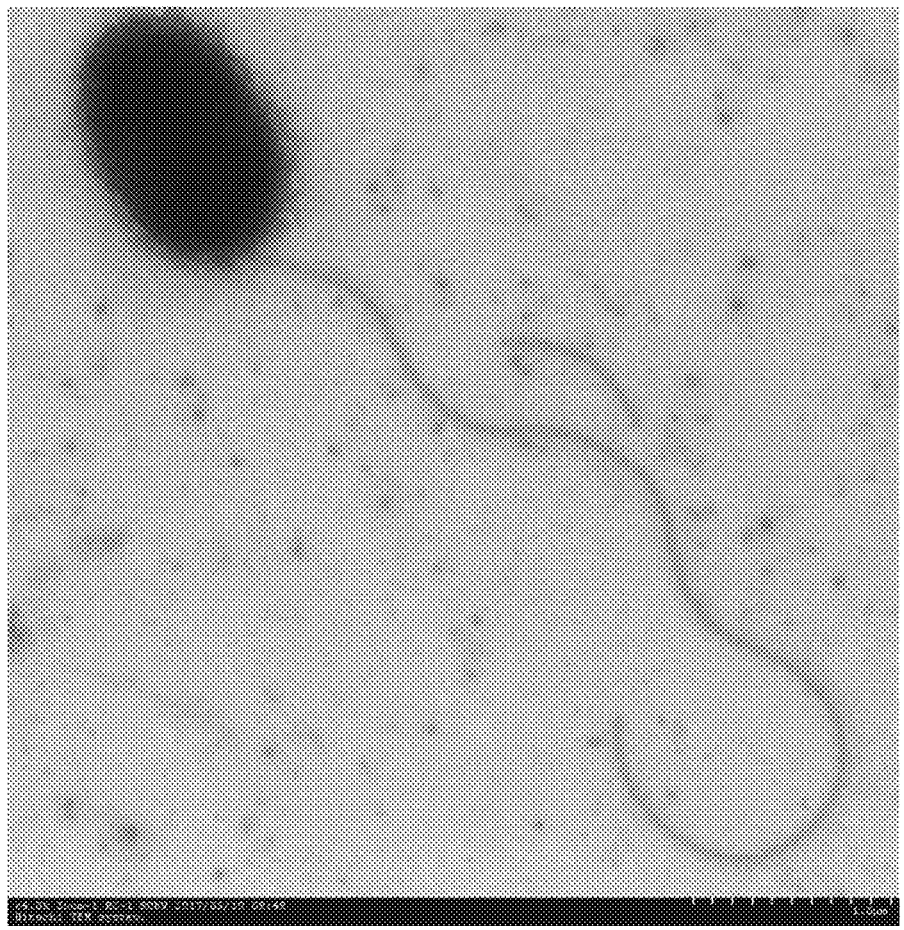

PSEUDOMONAS AERUGINOSA WITH MONOMETHYLAMINE DEGRADABILITY AND APPLICATION THEREOF

This application claims the priority of Chinese Patent Application No. 201710670248.2 that is entitled "Pseudomonas Aeruginosa with Monomethylamine Degradability and Application Thereof" and was submitted to the China Patent Office on Aug. 8, 2017. The entire contents are incorporated herein by reference.

FIELD OF THE INVENTION

The present invention belongs to the field of microbial technology, and more particularly relates to a strain of Pseudomonas aeruginosa with monomethylamine degradability and the application thereof. The Sequence Listing of which is titled "062188-00001_Sequence_Listing", the digital .txt file of the Sequence Listing having a file size of 2,648 bytes, created on Sep. 28, 2022 and filed herewith, is incorporated herein by reference as if fully set forth.

BACKGROUND OF THE INVENTION

Monomethylamine (MMA, $CH_3NH_2$) is a fatty amine malodorous compound with the simplest molecular structure. It has a low odor threshold and is difficult to be biodegraded. Its odor threshold is as low as 0.021 ppm, and its vapor pressure is 202.65 kPa at 25° C. It can produce strong irritating fish odor at low concentrations, and is easily absorbed by skin, respiratory tract and gastrointestinal tract. It has strong irritating and corrosive effects on eyes, skin and respiratory mucosa, as well as a sympathomimetic effect on the whole body. Besides, monomethylamine is also an organic chemical raw material used in all walks of life in the national economy, such as pesticides, solvents, medicines and photographic materials. The discharge of monomethylamine-containing wastewater into environmental water causes the water to become black, smelly and eutrophic, which makes the environment worse and worse, seriously affecting people's physical and mental health. At present, the physical and chemical treatment methods for monomethylamine at home and abroad mainly include adsorption, oxidation, photocatalysis, and the like. Compared with these physical and chemical methods, the use of microbial methods to degrade malodorous pollutants has the advantages of low cost, complete degradation and no secondary pollution, and has therefore been the focus of researchers at home and abroad. It has been reported that researchers have studied the degradation of monomethylamine by inoculating methylotrophic bacteria or mixed strains. However, the literature on the degradation of monomethylamine by using a separately cultured new single strain is very limited. Therefore, screening out high-efficiency, low-cost monomethylamine-degrading bacteria is of great significance in the purification of malodorous organic nitrogenous wastewater and waste gas. Pseudomonas is a Gram-negative bacterium, and sometimes in the shape of a rod or a line; on the surface of a solid medium, this bacterium can form green, round, and neatly edged colonies. According to the literature research, so far there have been no reports and patents on the use of Pseudomonas aeruginosa to degrade monomethylamine.

CONTENTS OF THE INVENTION

An object of the present invention is to overcome the deficiencies of the prior art and to provide a strain of Pseudomonas aeruginosa with monomethylamine degradability. Belonging to a new variant of Pseudomonas aeruginosa, the Pseudomonas aeruginosa GDUTAN1 has excellent monomethylamine degradability and can degrade monomethylamine in the environment at a high monomethylamine degradation efficiency.

Another object of the present invention is to provide an application of the above-described Pseudomonas aeruginosa with monomethylamine degradability in environmental remediation.

The objects of the present invention are achieved by the following technical solution:

The present invention, in a first aspect, provides a strain of Pseudomonas aeruginosa with monomethylamine degradability named Pseudomonas aeruginosa GDUTAN1, which was deposited on May 24, 2017 in the China Center for Type Culture Collection in Wuhan University, Wuhan City, Hubei Province with a deposit number of CCTCC NO.: M 2017283.

The morphological characteristics of the Pseudomonas aeruginosa with monomethylamine degradability of the present invention are as follows:

(a) By using the physiological and biochemical identification methods of bacteria and electron microscopy, it was revealed that the Pseudomonas aeruginosa screened out was Gram-negative and rod-like with cell staining.

(b) Morphological characteristics of the colonies: After 24 h of culture in an LB solid medium, the colony appeared to be round, green and opaque, having a diameter of 1-2 mm.

The main physiological and biochemical characteristics of the Pseudomonas aeruginosa with monomethylamine degradability of the present invention are shown in Table 1 below:

TABLE 1

Main physiological and biochemical characteristics of Pseudomonas aeruginosa

| Items | Test results |
| --- | --- |
| Arabinose | − |
| Xylose | − |
| Glucose | − |
| Mannitol | − |
| Citrate utilization | + |
| DNA hydrolysis | − |
| V-P test | − |
| Nitrate (reduction) | − |
| Siarch hydrolysis | − |
| Gelatin liquefaction | − |
| Anaerobic growth | + |
| 2% NaCl growth | + |
| 5% NaCl growth | + |
| pH = 5.5 growth | + |
| pH = 9.0 growth | + |
| Gram staining | − |
| 50° C. growth | − |
| 15° C. growth | + |

The 16S rDNA sequence of the Pseudomonas aeruginosa with monomethylamine degradability of the present invention is set forth in SEQ ID NO: 1.

By alignment analysis of the 16S rDNA sequence, the strain of the present invention was found to have up to 100% homology with Pseudomonas aeruginosa DSM 5007. By combining the morphological characteristics, growth conditions, physiological and biochemical identification results of the bacteria, it was determined that Pseudomonas aeruginosa GDUTAN1 belongs to a new variant of Pseudomonas aeruginosa and was named Pseudomonas aeruginosa GDUTAN1.

The present invention, in a second aspect, provides an application of the *Pseudomonas aeruginosa* with monomethylamine degradability in environmental remediation.

The *Pseudomonas aeruginosa* with monomethylamine degradability of the present invention is capable of degrading monomethylamine in the environment when used in environmental remediation.

Further, the environment includes the atmosphere, water or soil.

The use of the *Pseudomonas aeruginosa* GDUTAN1 of the present invention for the biodegradation of monomethylamine comprises the following preferred steps: Adjusting the pH of the substance containing monomethylamine to 5-9, and adding the enriched *Pseudomonas aeruginosa* GDUTAN1 bacterial solution in an inoculating amount of 0.5-2.5 mL, and then reacting at 20° C. to 40° C.;

the concentration of monomethylamine in the monomethylamine-containing substance is preferably 50-140 mg/L;

preferably, the reaction is carried out under oscillation conditions;

more preferably, the rate of oscillation is 100-250 rpm; and preferably, the reaction time is 96-108 h.

Compared with the prior art, the present invention has the following beneficial effects:

1. The strain of the present invention is *Pseudomonas aeruginosa GDUTAN1* with monomethylamine degradability, which was obtained by screening the landfill leachate of a landfill in Guangzhou City, Guangdong Province for the first time.

2. The *Pseudomonas aeruginosa* GDUTAN1 of the present invention has the ability to efficiently degrade monomethylamine; when it degraded monomethylamine for 96 h at a substrate concentration of 50-140 mg/L, the degradation efficiency could reach 99%.

BRIEF DESCRIPTION OF THE DRAWINGS

FIG. 1 shows the morphology of *Pseudomonas aeruginosa* GDUTAN1 of the present invention under an electron microscope.

DETAILED DESCRIPTION OF THE EMBODIMENTS

The content of the present invention is further illustrated by the following specific examples, but these examples should not be construed as limiting the present invention. The technical means used in the examples are conventional means well known to those skilled in the art unless otherwise specified. Unless otherwise indicated, the reagents, methods, and devices employed in the present invention are routine in the art.

Example 1

A strain of *Pseudomonas aeruginosa* with monomethylamine degradability, named *Pseudomonas aeruginosa* GDUTAN1, was deposited on May 24, 2017 in the China Center for Type Culture Collection in Wuhan University (No. 299 Bayi Road, Wuchang District, Wuhan City, Hubei Province) with a deposit number of CCTCC NO: M 2017283.

The *Pseudomonas aeruginosa* GDUTAN1 of the present example was isolated and screened from leachate of a landfill in Guangzhou City, Guangdong Province. The separation and purification methods were as follows: The acclimation medium used was an inorganic salt medium (g/L) (each 1000 mL of the inorganic salt medium contains: $K_2HPO_4.3H_2O$ 1.2 g, $KH_2PO_4$ 1.2 g, $NH_4Cl$ 0.4 g, $MgSO_4.7H_2O$ 0.2 g, and $FeSO_4.7H_2O$ 0.01 g; each 1 mL of the trace element solution contains: $CaCl_2.2H_2O$ 0.2 g, $MnSO_4.4H_2O$ 0.2 g, $CuSO_4.2H_2O$ 0.01 g, $ZnSO_4.7H_2O$ 0.2 g, $CoCl_2.6H_2O$ 0.09 g, $Na_2MoO_4.2H_2O$ 0.12 g, and $H_3BO_3$ 0.006 g). First, 1 mL of the landfill leachate was taken and diluted 100 times, inoculated into a nutrient broth, and aerobically cultured at 37° C. for 1 day in a shaker at a rotational speed of 150 rpm. 1 mL of the enriched bacterial solution was taken and inoculated in a nutrient solution containing monomethylamine, and aerobically cultured at 37° C. for 5 days in a shaker at a rotational speed of 150 rpm, and then moved to the next concentration in an inoculating amount of 10%, with the substrate acclimation gradients respectively at 10, 20, 50 and 100 mg/L. After acclimation, the acclimation solution was applied to a solid agar plate with monomethylamine as the sole carbon source (the solid medium containing monomethylamine was obtained by adding 18 g of agar and 4 mg of monomethylamine to per liter of the above inorganic salt medium), and cultured at 35° C. for 3 days; a single colony was selected and placed in a beef extract peptone medium (beef extract 3.0 g/L, peptone 10.0 g/L, NaCl 5.0 g/L, pH 7.4-7.6), and enriched and cultivated; the degradation efficiency of monomethylamine was determined, and the strain with the highest degradation efficiency was selected for purification.

Determination of degradation efficiency: Sampling periodically during the biodegradation of monomethylamine, and determining the degradation efficiency spectrophotometrically. Degradation efficiency=(initial concentration−final concentration)/initial concentration.

Spectrophotometric determination of monomethylamine concentration: Taking a certain amount of the monomethylamine degradation solution into a 10 mL colorimetric tube, diluting to 2.0 mL with an absorption solution (0.01 M HCl), and respectively adding 4.0 mL of buffer (obtained by dissolving 4.08 g of potassium dihydrogen phosphate and 1.6 g of borax in 80 mL of distilled water, adding 6.35 mL of 5.0 M NaOH solution, and diluting to 100 mL with water) and 0.4 mL of diazonium salt solution (obtained by adding 1.0 mL of sodium nitrite solution to 10 mL of p-nitrophenylamine hydrochloride solution and mixing), shaking well, letting stand for 40 min, adding 1.0 mL of 5 M NaOH solution, mixing, letting stand for 20 min, and performing colorimetric quantification at 510 nm.

The purified colonies were identified, with the results as follows:

(1) Morphological Characteristics of the Bacteria:

a. By using the conventional physiological and biochemical identification methods of bacteria and electron microscopy, it was revealed that the *Pseudomonas aeruginosa* screened out was Gram-negative with cell staining; under the electron microscope, the bacterium was rod-like with a single flagellum, and had a size of (0.5 to 0.9)×(0.5 to 1.5) μm, as shown in FIG. 1;

b. morphological characteristics of the colonies: after 24 h of culture in an LB solid medium, the colony appeared to be neatly edged, round, green and opaque, having a diameter of 1-2 mm; and c. the main physiological and biochemical characteristics of *Pseudomonas aeruginosa* are shown in Table 2:

TABLE 2

Physiological and biochemical characteristics
of *Pseudomonas aeruginosa*

| Items | Test results |
| --- | --- |
| Arabinose | − |
| Xylose | − |
| Glucose | + |
| Mannitol | − |
| Citrate utilization | + |
| DNA hydrolysis | − |
| V-P test | − |
| Nitrate (reduction) | − |
| Starch hydrolysis | − |
| Gelatin liquefaction | + |
| Anaerobic growth | + |
| 2% NaCl growth | + |
| 5% NaCl growth | + |
| pH = 5.5 growth | + |
| pH = 9.0 growth | + |
| Gram staining | − |
| 50° C. growth | − |
| 15° C. growth | + |

The above results indicate that the selected bacteria of the present invention had physiological and biochemical characteristics very similar to those of *Pseudomonas aeruginosa*.

(2) Extracting Bacterial Genomic DNA and Using Bacterial 16S rDNA Universal Primers:

```
Upstream primer: F27
(5'-AGTTTGATCMTGGCTCAG-3')

Downstream primer: R1492
(5'-GGTTACCTTGTTACGACTT-3')
```

The entire 16S rDNA gene was amplified, with the sequencing results as shown in SEQ ID NO: 1.

By aligning the 16S rRNA gene sequence of 1331 bp in length as shown in SEQ ID NO: 1 with the gene sequence registered in the Genbank, it was found that the strain had 100% homology with *Pseudomonas aeruginosa* DSM 5007.

Based on the above physiological and biochemical characteristics and 16S rRNA gene sequencing results, the selected strain of the present invention should belong to a new variant of *Bacillus*, and was named *Pseudomonas aeruginosa* GDUTAN1.

The *Pseudomonas aeruginosa* was deposited on May 24, 2017 in the China Center for Type Culture Collection (CCTCC) in Wuhan University (No. 299 Bayi Road, Wuchang District, Wuhan City, Hubei Province) with a deposit number of CCTCC NO: M 2017283.

Example 2

This example is the application of *Pseudomonas aeruginosa* GDUTAN1 in environmental remediation, which can degrade monomethylamine in the environment. The environment includes the atmosphere, water or soil.

The method for verifying the monomethylamine degradability of the selected *Pseudomonas aeruginosa* GDUTAN1 of the present invention is as follows:

Inoculating the *Pseudomonas aeruginosa* GDUTAN1 strain in the slant preservation into an LB enrichment culture solution, activating the bacteria at 35° C. for 24 h in a shaker at 150 rpm, and centrifuging the bacterial solution, and then collecting the bacteria. Resuspending with 5 mL of an inorganic salt solution (each 100 mL of the inorganic salt solution contains the following components: $K_2HPO_4 \cdot 3H_2O$ 0.12 g, $KH_2PO_4$ 0.12 g, $NH_4Cl$ 0.04 g, $MgSO_4 \cdot 7H_2O$ 0.02 g, $FeSO_4 \cdot 7H_2O$ 0.001 g, $CaCl_2 \cdot 2H_2O$ 0.02 g, $MnSO_4 \cdot 4H_2O$ 0.02 g, $CuSO_4 \cdot 2H_2O$ 0.001 g, $ZnSO_4 \cdot 7H_2O$ 0.02 g, $CoCl_2 \cdot 6H_2O$ 0.009 g, $Na_2MoO_4 \cdot 2H_2O$ 0.012 g, $H_3BO_3$ 0.0006 g, and double distilled water 100 mL), and inoculating 2.0 mL of the bacterial solution into 100 mL of an inorganic salt solution containing 50 mg/L of monomethylamine, with the pH of the inorganic salt at 6; reacting at 35° C. for 96 h in a shaker at 200 rpm, sampling periodically and determining the degradation efficiency spectrophotometrically. The degradation efficiency, measured in the same way as in Example 1, was determined to be 99.2%.

Example 3

Inoculating the *Pseudomonas aeruginosa* GDUTAN1 strain in the slant preservation into an LB enrichment culture solution, activating the bacteria at 35° C. for 24 h in a shaker at 150 rpm, and centrifuging the bacterial solution, and then collecting the bacteria. Resuspending with 5 mL of an inorganic salt solution, and inoculating 2.0 mL of the bacterial solution into 100 mL of an inorganic salt solution containing 50 mg/L of monomethylamine (the same as in Example 2), with the pH of the inorganic salt at 8; reacting at 35° C. for 96 h in a shaker at 100 rpm, sampling periodically and determining the degradation efficiency spectrophotometrically. The degradation efficiency, measured in the same way as in Example 1, was determined to be 41.5%.

Example 4

Inoculating the *Pseudomonas aeruginosa* GDUTAN1 strain in the slant preservation into an LB enrichment culture solution, activating the bacteria at 35° C. for 24 h in a shaker at 150 rpm, and centrifuging the bacterial solution, and then collecting the bacteria. Resuspending with 5 mL of an inorganic salt solution, and inoculating 1.5 mL of the bacterial solution into 100 mL of an inorganic salt solution containing 80 mg/L of monomethylamine (the same as in Example 2), with the pH of the inorganic salt at 7; reacting at 20° C. for 96 h in a shaker at 150 rpm, sampling periodically and determining the degradation efficiency spectrophotometrically. The degradation efficiency, measured in the same way as in Example 1, was determined to be 98.9%.

Example 5

Inoculating the *Pseudomonas aeruginosa* GDUTAN1 strain in the slant preservation into an LB enrichment culture solution, activating the bacteria at 35° C. for 24 h in a shaker at 150 rpm, and centrifuging the bacterial solution, and then collecting the bacteria. Resuspending with 5 mL of an inorganic salt solution, and inoculating 2.0 mL of the bacterial solution into 100 mL of an inorganic salt solution containing 110 mg/L of monomethylamine (the same as in Example 2), with the pH of the inorganic salt at 6; reacting at 25° C. for 96 h in a shaker at 200 rpm, sampling periodically and determining the degradation efficiency spectrophotometrically. The degradation efficiency, measured in the same way as in Example 1, was determined to be 99.9%.

Example 6

Inoculating the *Pseudomonas aeruginosa* GDUTAN1 strain in the slant preservation into an LB enrichment culture solution, activating the bacteria at 35° C. for 24 h in a shaker at 150 rpm, and centrifuging the bacterial solution, and then collecting the bacteria. Resuspending with 5 mL of an inorganic salt solution, and inoculating 1.5 mL of the bacterial solution into 100 mL of an inorganic salt solution containing 140 mg/L of monomethylamine (the same as in Example 2), with the pH of the inorganic salt at 7; reacting at 30° C. for 96 h in a shaker at 150 rpm, sampling periodically and determining the degradation efficiency spectrophotometrically. The degradation efficiency, measured in the same way as in Example 1, was determined to be 99.0%.

The above examples are preferred embodiments of the present invention, but the embodiments of the present invention are not limited thereto, and any other alterations, modifications, substitutions, combinations, and simplifications made without departing from the spirit and principle of the present invention should all be equivalent replacements and included in the scope of protection of the present invention.

```
                              Sequence Listing

110   Guangdong University of Technology
    120   Pseudomonas aeruginosa with monomethylamine degradability and
          application thereof
    130   OP180087
    160   1
    170   SIPOSequenceListing 1.0
    210   1
    211   1331
    212   DNA
    213   Pseudomonas aeruginosa
    400   1 attcagcggc ggacgggtga gtaatgccta ggaatctgcc tggtagtggg ggataacgtc      60
cggaaacggg cgctaatacc gcatacgtcc tgagggagaa agtgggggat cttcggacct     120
cacgctatca gatgagccta ggtcggatta gctagttggt ggggtaaagg cctaccaagg     180
cgacgatccg taactggtct gagaggatga tcagtcacac tggaactgag acacggtcca     240
gactcctacg ggaggcagca gtggggaata ttggacaatg ggcgaaagcc tgatccagcc     300
atgccgcgtg tgtgaagaag gtcttcggat tgtaaagcac tttaagttgg gaggaagggc     360
agtaagttaa taccttgctg ttttgacgtt accaacagaa taagcaccgg ctaacttcgt     420
gccagcagcc gcggtaatac gaagggtgca agcgttaatc ggaattactg ggcgtaaagc     480
gcgcgtaggt ggttcagcaa gttggatgtg aaatccccgg gctcaacctg gaactgcat      540 ccaaaactac tgagctagag tacggtagag ggtggtggaa tttcctgtgt agcggtgaaa     600
tgcgtagata taggaaggaa caccagtggc gaaggcgacc acctggactg atactgacac     660
tgaggtgcga aagcgtgggg agcaaacagg attagatacc ctggtagtcc acgccgtaaa     720
cgatgtcgac tagccgttgg gatccttgag atcttagtgg cgcagctaac gcgataagtc     780
gaccgcctgg ggagtacggc cgcaaggtta aaactcaaat gaattgacgg gggcccgcac     840
aagcggtgga gcatgtggtt taattcgaag caacgcgaag aaccttacct ggccttgaca     900
tgctgagaac tttccagaga tggattggtg ccttcgggaa ctcagacaca ggtgctgcat     960
ggctgtcgtc agctcgtgtc gtgagatgtt gggttaagtc ccgtaacgag cgcaacccett   1020 gtccttagtt accagcacct cgggtgggca ctctaaggag actgccggtg acaaaccgga    1080
ggaaggtggg gatgacgtca agtcatcatg gcccttacgg ccagggctac acacgtgcta    1140
caatggtcgg tacaaagggt tgccaagccg cgaggtggag ctaatcccat aaaaccgatc    1200
gtagtccgga tcgcagtctg caactcgact gcgtgaagtc ggaatcgcta gtaatcgtga    1260
atcagaatgt cacggtgaat acgttcccgg gccttgtaca ccgcccgt cacaccatgg      1320 gagtgggttg c                                                         1331
```

The invention claimed is:

1. A method of degrading monomethylamine, comprising:

adjusting the pH of a substance containing monomethylamine to 5-9;

adding to the substance an isolated or purified strain of *Pseudomonas aeruginosa* named GDUTAN1, the strain deposited on May 24, 2017 in the China Center for Type Culture Collection in Wuhan University, Wuhan City, Hubei Province with a deposit number of CCTCC NO: M 2017283, in an inoculating amount of 0.5-2.5 mL; and reacting the substance and the strain of *Pseudomonas aeruginosa* at 20° C. to 40° C. to thereby degrade monomethylamine in the substance.

2. The method according to claim 1, wherein the substance comprises, water or soil.

* * * * *

SEQUENCE LISTING

<160> NUMBER OF SEQ ID NOS: 3

<210> SEQ ID NO 1
<211> LENGTH: 1331
<212> TYPE: DNA
<213> ORGANISM: Pseudomonas aeruginosa

<400> SEQUENCE: 1

```
attcagcggc ggacgggtga gtaatgccta ggaatctgcc tggtagtggg ggataacgtc      60
cggaaacggg cgctaatacc gcatacgtcc tgagggagaa agtgggggat cttcggacct     120
cacgctatca gatgagccta ggtcggatta gctagttggt ggggtaaagg cctaccaagg     180
cgacgatccg taactggtct gagaggatga tcagtcacac tggaactgag acacggtcca     240
gactcctacg ggaggcagca gtggggaata ttggacaatg ggcgaaagcc tgatccagcc     300
atgccgcgtg tgtgaagaag gtcttcggat tgtaaagcac tttaagttgg gaggaagggc     360
agtaagttaa taccttgctg ttttgacgtt accaacagaa taagcaccgg ctaacttcgt     420
gccagcagcc gcggtaatac gaagggtgca agcgttaatc ggaattactg ggcgtaaagc     480
gcgcgtaggt ggttcagcaa gttggatgtg aaatccccgg gctcaacctg gaactgcat      540
ccaaaactac tgagctagag tacggtagag ggtggtggaa tttcctgtgt agcggtgaaa     600
tgcgtagata taggaaggaa caccagtggc gaaggcgacc acctggactg atactgacac     660
tgaggtgcga aagcgtgggg agcaaacagg attagatacc ctggtagtcc acgccgtaaa     720
cgatgtcgac tagccgttgg gatccttgag atcttagtgg cgcagctaac gcgataagtc     780
gaccgcctgg ggagtacggc cgcaaggtta aaactcaaat gaattgacgg gggcccgcac     840
aagcggtgga gcatgtggtt taattcgaag caacgcgaag aaccttacct ggccttgaca     900
tgctgagaac tttccagaga tggattggtg ccttcgggaa ctcagacaca ggtgctgcat     960
ggctgtcgtc agctcgtgtc gtgagatgtt gggttaagtc cgtaacgag cgcaacccctt    1020
gtccttagtt accagcacct cgggtgggca ctctaaggag actgccggtg acaaaccgga    1080
ggaaggtggg gatgacgtca agtcatcatg gcccttacgg ccagggctac acacgtgcta    1140
caatggtcgg tacaaagggt tgccaagccg cgaggtggag ctaatcccat aaaaccgatc    1200
gtagtccgga tcgcagtctg caactcgact gcgtgaagtc ggaatcgcta gtaatcgtga    1260
atcagaatgt cacggtgaat acgttcccgg gccttgtaca caccgcccgt cacaccatgg    1320
gagtgggttg c                                                        1331
```

<210> SEQ ID NO 2
<211> LENGTH: 18
<212> TYPE: DNA
<213> ORGANISM: Artificial Sequence
<220> FEATURE:
<223> OTHER INFORMATION: Bacterial 16S rDNA upstream primer F27

<400> SEQUENCE: 2

```
agtttgatcm tggctcag                                                   18
```

<210> SEQ ID NO 3
<211> LENGTH: 19
<212> TYPE: DNA
<213> ORGANISM: Artificial Sequence
<220> FEATURE:
<223> OTHER INFORMATION: Bacterial 16S rDNA downstream primer R1492

<400> SEQUENCE: 3

```
ggttaccttg ttacgactt                                                  19
```